United States Patent [19]

Neri et al.

[11] 4,329,364

[45] May 11, 1982

[54] ANTIANDROGENIC AGENTS AND METHODS FOR THE TREATMENT OF ANDROGEN DEPENDENT DISEASE STATES

[75] Inventors: Rudolph O. Neri, Hawthorne; John G. Topliss, West Caldwell, both of N.J.

[73] Assignee: Schering Corporation, Kenilworth, N.J.

[21] Appl. No.: 725,821

[22] Filed: Sep. 23, 1976

Related U.S. Application Data

[60] Division of Ser. No. 505,116, Sep. 11, 1974, Pat. No. 3,995,060, and a continuation-in-part of Ser. No. 264,655, Jun. 20, 1972, abandoned, which is a continuation-in-part of Ser. No. 146,461, May 24, 1971, abandoned, which is a continuation-in-part of Ser. No. 876,999, Nov. 14, 1969, abandoned, which is a continuation-in-part of Ser. No. 734,854, Jun. 6, 1968, abandoned, which is a continuation-in-part of Ser. No. 573,836, Aug. 22, 1966, abandoned.

[51] Int. Cl.$^3$ ............................................ A61K 31/165
[52] U.S. Cl. .................................................. 424/324
[58] Field of Search .................. 510/505, 116; 424/324

Primary Examiner—Jerome D. Goldberg
Attorney, Agent, or Firm—Paul H. Ginsburg; Bruce M. Eisen

[57] ABSTRACT

This application relates to treatment of prostatic carcinoma with 4'-nitro-3'-trifluoromethylisobutyranilide.

1 Claim, No Drawings

ANTIANDROGENIC AGENTS AND METHODS FOR THE TREATMENT OF ANDROGEN DEPENDENT DISEASE STATES

This is a division of application Ser. No. 505,116 filed Sept. 11, 1974, now U.S. Pat. No. 3,995,060, and a continuation-in-part of our copending application, Ser. No. 264,655, filed June 20, 1972 now abandoned, which in turn, is a continuation-in-part of application Ser. No. 146,461, filed May 24, 1971, (now abandoned), which in turn, is a continuation-in-part of application, Ser. No. 876,999, filed Nov. 14, 1969 (now abandoned), which in turn, is a continuation-in-part of application, Ser. No. 734,854, filed June 6, 1968 (now abandoned), which in turn, is a continuation-in-part of application, Ser. No. 573,836, filed Aug. 22, 1966 (now abandoned).

This invention relates to valuable therapeutically active chemical compositions belonging to the general class of substituted anilides and to the processes for making and using such therapeutically effective compositions.

The invention sought to be patented, in one of its composition of matter aspects, is described as residing in the concept of a therapeutically effective quantity of a substituted anilide in admixture with a pharmaceutical carrier.

The invention sought to be patented, in one of its process aspects, is described as residing in the concept of using 4'-nitro-3'-trifluoromethylisobutyranilide in admixture with a pharmaceutical carrier, for the prevention and/or treatment of prostatic carcinoma. 4'-nitro-3'-trifluoromethylisobutyranilide possesses the inherent applied-use characteristics of exerting an antiandrogenic response when administered within the dose range of about 0.1 mg. to about 50 mg. per kg. of body weight per day and thus is useful in treating, alleviating and/or palliation of androgen-caused and/or androgen-dependent conditions such as prostatic hyperlasia (e.g. benign prostatic hypertrophy, prostatic carcinoma) the Stein-Leventhal syndrone, idiopathic hirsutism, acne, and the like. Additionally, the antiandrogenic characteristics of 4'-nitro-3'-trifluoromethylisobutyranilide has interesting veterinary-use application.

A particularly useful aspect of the foregoing is the application of the 4'-nitro-3'-trifluoromethylisobutyranilide for the treatment of prostatic carcinoma. As is well known, methods which have heretofore been employed for the treatment of prostatic carcinoma have met with little or no significant success. In studies concerning the treatment of prostatic carcinoma it has been found, particularly in the cases of estrogen therapy, that although there is a modest palliative response, the well-known estrogenic side effects often preclude long-term medical management. Alternative surgical intervention, i.e., orchiectomy, likewise provides only palliation which is often not maintained. Furthermore, orchiectomy also poses a psychologic trauma to the patient. Thus, the prevention, alleviation, palliation, and/or treatment of prostatic carcinoma, either in its localized stage, invasive state or in its distant metastatic stage (i.e., that stage wherein the cancerous cells have spread to body organs other than the prostate) with chemical agents, in the absence of concomitant side effects, is a goal long sought.

We have found from numerous laboratory tests with the compounds of this invention, and by initial clinical observations with 4'-nitro-3'-trifluoromethylisobutyranilide, that 4'-nitro-3'-trifluoromethylisobutyranilide is a chemotherapeutic agent for the treatment of prostatic carcinoma. Indeed, it is thought to prevent and/or delay the onset and spread of prostatic carcinoma. Thus, an essence of this invention is the employment of 4'-nitro-3'-trifluoromethylisobutyranilide, in combination with a pharmaceutical carrier, particularly in formed dosage units suitable for therapeutic application, to delay and/or prevent the onset of prostatic carcinoma, and to treat mammals suffering from prostatic carcinoma, said carcinoma being either localized, invasive, or distant metastatic stage; this latter aspect, of course, embracing the concept of treating the carcinoma appearing in areas of the body other than the prostate, but which by virtue of its cellular make-up, has its origin in the prostate. In the application of 4'-nitro-3'-trifluoromethylisobutyranilide for the uses just described, on the basis of standard laboratory techniques designed for determining efficacy and safety, this compound will be suitable for use in the dose range of about 0.1 mg. to about 50 mg. per kg. of body weight per day. Usually, depending upon the severity of the condition, a satisfactory therapeutic response will be achieved in those mammal species having an adult body weight of approximately 70 kg. when 1 to 4 daily dosage units of formed pharmaceutical formulations are administered to the species. Thus, a suitable dosage range for 70 kilogram mammal is in the range of about 7 mg. to 3500 mg. of the preferred active ingredients per day until symptomatic relief is obtained as ascertained by the attending diagnostician.

In one of its more important aspects then, the instant invention may be described as residing in the concept of administering a therapeutic formulation containing as the essential ingredient, 4'-nitro-3'-trifluoromethylisobutyranilide to a mammal for the purpose of delaying and/or preventing the onset of prostatic carcinoma as well as in the treatment of mammals already afflicted with prostatic carcinoma.

In those species afflicted with prostatic hypertrophy the frequency of the hypertrophic condition seems to increase with increasing age and thus represents a serious problem, even among older canine household pets. In general, hormone therapy, such as for example, administration of estrogenic substances, has not proved to be a particularly desirable treatment, not only because of the undesirable side effects due to the inherent properties of the estrogens, but also because such agents have not proved to be fully efficacious in providing meaningful remissions and cures. Surgical ablation, even though effective, is also not particularly desirable for in addition to the expected 2–3% mortality rate, many patients experience such non-fatal complications such as epididymitis, pneumonia, pyelonephritis, secondary resection, etc. Thus, the chemotherapeutic treatment of prostatic hypertrophy with concomitant absence of side effects induced by the anti-androgenic agent is also a goal long sought.

It has been determined by standard laboratory test procedures that the compounds of this invention produce marked remissions in cases of prostatic hyperlasia without the undesirable effects elicited upon the administration of estrogens or complications inherent in any surgical procedures. Usually, depending upon the severity of the condition, a satisfactory therapeutic response is achieved in those mammal species having an adult body weight of approximately 70 kg. when 1 to 4 dosage units of a formed pharmaceutical formulation containing a compound of this invention is administered to the species. Thus a suitable dosage range for a 70 kilogram mammal is in the range of about 25 mg. to 500 mg. of the preferred active ingredients per day until symptomatic relief is obtained as ascertained by the attending diagnostician.

In addition to the aforementioned applied uses, the compounds of this invention (I) also are especially valuable for veterinary uses. For example, the administration of 4'-nitro-3'-trifluoromethylisobutyranilide of this invention is useful in reducing androgen-caused odor normally associated with the meat of male animal species, in controlling and/or eliminating the birth of normal males, and for reducing the aggressive tendencies of the male animal species; these actions of course being dependent largely on the time of administration of the anti-androgenic agent.

As stated, 4'-nitro-3'-trifluoromethylisobutyranilide of this invention may be used as chemical castrating agents in the veterinary field. It has been long known that male bovine and porcine species are not particularly suitable as meat producing animals. It is also known that the male animal grows at a faster rate, usually weighs more and produces a leaner carcass than does the corresponding female species. One attempt at converting the male into a more suitable commercial meat source has been by surgical castration (i.e. removal of the androgen source). However, this method has not been completely satisfactory for it involves a time-consuming process and often times leads to post-surgical problems such as infections.

In its generic process aspect then, the instant invention may be described as residing in the concept of exerting an antiandrogenic effect which comprises administering a therapeutic formulation containing as the essential ingredient, 4'-nitro-3'-trifluoromethylisobutyranilide.

It is recognized that certain anilides have been known to exert untoward side effects in their use as chemotherapeutic agents. For example, it is known that at certain doses, certain anilides will cause methemoglobin formation and sulfhemobloginemia and appropriate laboratory tests are readily available to the art to determine the dosage at which these untoward side effects will be manifest (Goodman and Gilman, 1955, MacMillan Company). It is a discovery connected with 4'-nitro-3'-trifluoromethylisobutyranilide that the untoward side effects do not occur at the effective dosage range wherein the compound exerts its beneficial antiandrogenic effects and thus this compound is extremely useful for the purposes herein described. In the determination of the dosage range at which the untoward side effects will begin to appear, standard laboratory procedures may be applied. In general, the untoward side effects, if caused by the preferred compound of this invention, are seen at doses well above the 50 mg./kg. of body weight. However, in all instances there is a sufficient difference between the therapeutic dosage and the dosage wherein toxic manifestations are elicited and thus 4'-nitro-3'-trifluoromethylisobutyranilide possesses a suitable therapeutic index.

In its subgeneric concepts the instant invention relates to the application of 4'-nitro-3'-trifluoromethylisobutyranilide to mammals for the treatment of benign prostatic hypertrophy, acne, hirsutism, and other androgen-dependent body malfunctions and to its use in the aforementioned veterinary application. In another subgeneric concept, the instant invention relates to the appliction of 4'-nitro-3'-trifluoromethylisobutyranilide to mammals for the treatment of prostatic carcinoma.

4'-nitro-3'-trifluoromethylisobutyranilide can be administered orally in the form of tablets, capsules, elixirs, and the like or may be administered by parenteral injection. Additionally, compound may be administered in the form of suppositories (both rectal and urethral) and lotions. In tablet form it is compounded with an inert pharmaceutical carrier which may contain a suitable binder such as, for example, gums, starches, and sugars. It may also be incorporated into gelatin capsules or formulated into elixirs which have the advantage of being susceptible to manipulations in flavor by the addition of standard natural or synthetic flavoring agents. Highly satisfactory administration may also be achieved in the form of aqueous parenteral suspension. 4'-nitro-3'-trifluoromethylisobutyranilide effectively elicits an antiandrogenic effect at about 1 to about 50 mg./kg. of body weight on a daily basis. Preferably, these formulations are so proportioned as to afford a unit dosage of from about 1 to about 100 mg. of active substituted-anilide. Particularly preferred are unit dosages ranging from about 5 to about 25 mg. Preferably, the compound is administered orally.

Furthermore, the therapeutically active ingredient may be admixed with the food of the species to which the administration is desired, thereby obtaining a therapeutically efficacious dose level.

Representative embodiments of the formulations containing the compositions of this invention are as follows:

| TABLET FORMULATIONS | |
|---|---|
| | Milligrams per Tablet |
| Formula A (5 mg.) | |
| 4'-nitro-3'-trifluoromethyl-isobutyranilide | 5.0 |
| Starch, Food Grade | 5.0 |
| Lactose, U.S.P. (Spray Dried) | 89.0 |
| Magnesium Stearate, U.S.P. | 0.5 |
| | 100.0 |
| Formula B (25 mg.) | |
| 4'-nitro-3'-trifluoromethyl-isobutyranilide | 25.0 |
| Starch, Food Grade | 10.0 |
| Lactose, U.S.P. (Spray Dried) | 164.0 |
| Magnesium Stearate, U.S.P. | 1.0 |
| | 200.0 |

Blend the milled 4'-nitro-3'-trifluoromethylisobutyranilide with the starch in a suitable mixing vessel. Add an equal weight of the spray dried lactose to the blend and mix until uniform. Combine the resultant blend with the remainder of the spray dried lactose and mix until uniform. Charge the magnesium stearate with a portion of the active tablet mix and blend. Blend the magnesium stearate mix with the remaining active tablet base. Continue mixing until uniform. Compress to target weight (100.0 mg. for 5 mg. tablet and 200.0 mg. for 25 mg. tablet).

FORMULA AND METHOD OF MANUFACTURE FOR 4'-NITRO-3'-TRIFLUORO-METHYLISOBUTYRANILIDE CAPSULES IN 10, 25, 50, 100, 150 AND 200 MG. DOSAGE UNITS

| FORMULA | MG./CAPSULE | | | | | |
|---|---|---|---|---|---|---|
| 4'-Nitro-3'-trifluoro-methylisobutyranilide* (Milled) | 10.00 | 25.00 | 50.00 | 100.00 | 150.00 | 200.00 |
| Lactose | 375.00 | 360.00 | 335.00 | 285.00 | 235.00 | 185.00 |
| Sodium Lauryl Sulfate | 12.00 | 12.00 | 12.00 | 12.00 | 12.00 | 12.00 |
| Polyvinylpyrrolidone (PVP) | 25.00 | 25.00 | 25.00 | 25.00 | 25.00 | 25.00 |
| S.D. Alcohol, 3-A** | — | — | — | — | — | — |
| Corn Starch | 77.00 | 77.00 | 77.00 | 77.00 | 77.00 | 77.00 |
| Magnesium Stearate | 1.00 | 1.00 | 1.00 | 1.00 | 1.00 | 1.00 |
| Fill Weight (mg.) | 500.00 | 500.00 | 500.00 | 500.00 | 500.00 | 500.00 |

*Mixed with chunks of dry ice and passed through Fitzmill using either No. 1A or 2 screen, impact forward and fast speed. Tray and dry overnight at 40° C. (5–240 microns).
**Approximately 75 ml. 3-A alcohol/100 capsules; or 60 ml. water/1000 capsules.

METHOD OF MANUFACTURE

1. Blend the 4'-nitro-3'-trifluoromethylisobutyranilide, lactose and sodium lauryl sulfate together in a suitable size mixing bowl for 20–30 minutes.
2. Pass mixed powders from Step 1 through suitable comminuting machine (Raymond Mill with Herringbone screen or Fitzmill with No. 0 screen, impact forward and fast speed).
3. Determine percent of milled powders recovered. Recharge milled powders to mixing bowl and blend for 5–10 minutes.
4. Dissolve polyvinylpyrrolidone in approximately 90% of the specified quantity of 3-A alcohol (or water).
5. Granulate the milled powders from Step 3 with the PVP-alcoholic solution from Step 4 using the balance of the specified 3-A alcohol as a rinse, to a uniform pasty mass (use additional 3-A alcohol if necessary).
6. Back granulate the pasty mass with corn starch, continue mixing until uniform damp granules are formed.
7. Pass damp granulation through No. 12 screen by hand (¼" screen on Fitzmill, knives forward and medium speed).
8. Spread onto trays and dry in oven for 14–16 hours at 40° C. or 50° C. for water.
9. Reduce dried granulation through No. 40 mesh screen (No. 30 mesh on Fitzmill, impact forward and fast speed).
10. Determine percent of granulation recovered.
11. Add corrected quantity of magnesium stearate and blend for 2–3 minutes.
12. Fill into capsules.

We claim:
1. A method for the treatment of prostatic carcinoma which comprises administering to a mammal suffering from prostatic carcinoma a therapeutically effective quantity of 4'-nitro-3'-trifluoromethylisobutyranilide.

* * * * *

UNITED STATES PATENT AND TRADEMARK OFFICE

CERTIFICATE EXTENDING PATENT TERM
UNDER 35 U.S.C. 156

Patent No.    : 4,329,364

Dated         : May 11, 1982

Inventor(s)   : Rudolph Neri et al

Patent Owner  : Schering Corporation

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 25th day of January 1990.

Jeffrey M. Samuels
Acting Commissioner of
    Patents and Trademarks